United States Patent [19]

Chen et al.

[11] Patent Number: 5,103,038

[45] Date of Patent: Apr. 7, 1992

[54] SUBSTITUTED CYCLOPENTADIENE ELECTRON TRANSPORT COMPOUNDS

[75] Inventors: Chin H. Chen, Fairport, N.Y.; John L. Fox, Baltimore, Md.; Yann Hung, Rochester, N.Y.

[73] Assignee: Eastman Kodak Company, Rochester, N.Y.

[21] Appl. No.: 438,813

[22] Filed: Nov. 20, 1989

[51] Int. Cl.$^5$ ............... C07C 255/31; C07C 255/50
[52] U.S. Cl. ............................ 558/426; 558/419; 568/928; 570/129
[58] Field of Search ............ 558/426, 419; 568/928; 570/129

[56] References Cited

U.S. PATENT DOCUMENTS 4,082,550 4/1978 Yoerger ........................ 430/83

FOREIGN PATENT DOCUMENTS 0069397 12/1983 European Pat. Off. .

OTHER PUBLICATIONS

C. A. vol. 77 (1972), 4655e McBee et al.
C.A. 1972–1976 Formula Index, p. 9533F.

*Primary Examiner*—Joseph Paul Brust
*Attorney, Agent, or Firm*—Dressler, Goldsmith, Shore, Sutker & Milnamow, Ltd.

[57] ABSTRACT

Novel tetrasubstituted dicyanomethylene cyclopentadienes are provided which have utility as electron-transport agents in positively-charged electrophotographic elements. The compounds are characterized by the formula:

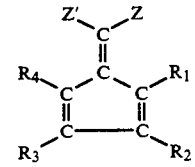

wherein:
  $R_1$ and $R_4$ are each independently selected from the group consisting of lower alkyl, halogen and cyano;
  $R_2$ and $R_3$ are each independently selected from the group consisting of aryl and substituted aryl; and
  Z and Z' are each an electron withdrawing group.

3 Claims, No Drawings

SUBSTITUTED CYCLOPENTADIENE ELECTRON TRANSPORT COMPOUNDS

FIELD OF THE INVENTION

This invention is in the field of substituted cyclopentadiene compounds useful as electron transport compounds in photoconductor elements.

BACKGROUND OF THE INVENTION

U.S. Pat. No. 4,082,550 describes heterogeneous photoconductive compositions comprised of particles of an organic photoconductor that is chemically sensitized with a monomeric hexachlorocyclopentene and dispersed in a cellulose nitrate binder.

European Patent Application No. 0/069 397 describes an electrophotographic plate having a charge generating layer and a charge transporting layer, on an electrically conductive substrate. The charge transporting layer incorporates a dicyano vinyl compound in combination with an electron donating compound.

In photoconductor elements of the type employing a charge generating layer and a charge transporting layer, it has been common to employ in the charge transporting layer either a polymer, such as polyvinyl carbazole, or a composition comprised of an electron-donating, charge transporting, low molecular weight organic compound dissolved in an insulating binder polymer. These charge transporting layers commonly suffer from one or more problems, such as high dark decay, insufficient electron charge transport activity, fluctuations in surface potential upon repeated use, decreasing sensitivity with repeated use, and a gradually increasing residual potential upon repeated use. Consequently, new electron-transport agents that exhibit sufficient sensitivity, but do not exhibit disadvantages such as above indicated would be desirable for us in positively charged photoconductor elements.

So far as now known, no one has heretofore proposed the use of tetrasubstituted, dicyano vinyl substituted cyclopentadienes as electron-transport agents.

SUMMARY OF THE INVENTION

This invention relates to certain new tetrasubstituted dicyanomethylene cyclopentadienes and to the use of such compounds as electron-transport agents in charge transport layers of photoconductor elements, especially as electron-transport agents in positively-charged photoconductor elements.

The tetrasubstituted dicyanomethylene cyclopentadienes of the present invention are characterized by the formula:

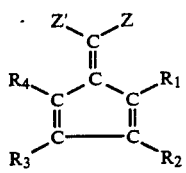
(1)

wherein:

$R_1$ and $R_4$ are each independently selected from the group consisting of lower alkyl, halogen, and cyano;

$R_2$ and $R_3$ are each independently selected from aryl and substituted aryl groups; and Z and Z' are each an electron withdrawing group.

Suitable electron withdrawing groups include cyano, nitro, sulfone, ester, ketone and trifluoromethyl groups.

Presently preferred compounds of Formula (1) are those wherein Z and Z' are each cyano, $R_2$ and $R_3$ are each phenyl, and $R_1$ and $R_4$ are each methyl or ethyl.

The compounds of Formula (1) when used as electron-transport agents in charge transport layers of positively charged photoconductor elements display low dark decay and improved sensitivity.

The compounds of Formula (1) can be used with conventional electrically conductive layers and charge generation layers known to the art.

Thus, the present invention also relates to new multiactive photoconductor elements which employ in a charge transport layer at least one compound of Formula (1) dissolved in an organic, polymeric, electrically insulating binder.

Other and further aims, purposes, features, advantages, and the like will be apparent to those skilled in the art from the teachings of the present specification taken with the appended claims.

DETAILED DESCRIPTION OF THE INVENTION

The term "lower" as used herein in reference to a group, such as alkyl, or the like, means that such group contains less than 7 carbon atoms.

The term "aryl" or "aryl group" as used herein means both unsubstituted aryl groups containing 6 to 14 carbon atoms, such as phenyl or naphthyl, and also substituted aryl groups.

The term "substituted" as used herein in reference to a group, such as an aryl group, or the like, means that such group is itself substituted by a group, such as lower alkyl; lower alkylene; nitro; halo; primary, secondary, or tertiary amino; cyano; sulfate; and the like provided that such so substituted group contains a total number of carbon atoms within the range specified therefor.

The term "halogen" as used herein means fluorine, chlorine, bromine or iodine.

Compounds of Formula (1) can be prepared by any convenient procedure. However, a presently preferred procedure is to admix with tetrahydrofuran (preferably freshly distilled) a solution of titanium tetrachloride in carbon tetrachloride. Preferably the carbon tetrachloride has been purified by passage through 4 Å molecular sieves. At the time of the admixture, the temperature is maintained below about 0° C. under oxygen-free, anhydrous, liquid-phase conditions. For example, anhydrous reactants under a nitrogen blanket can be used. The mole ratio of the tetrahydrofuran to the titanium tetrachloride is in the range of about 1:2 to about 1:4.

A precipitate is thus formed as a $TiCl_4$-THF complex. Thereafter, without separation from the liquid phase, the precipitate is admixed with a solution of tetrahydrofuran containing a 2,5-di(lower alkyl)-3,4-di(aryl)cyclopentadienone and malonitrile at a temperature below about 0° C. under oxygen-free, anhydrous conditions. The mole ratio of the 2,5-di(lower alkyl)-3,4-di(aryl)cyclopentadienone to the malonitrile is in the range of about 1:1 to about 1:2, and the mole ratio of the titanium tetrachloride to the malonitrile is in the range of about 2:1 to about 4:1.

The 2,5-di(lower alkyl)-3,4-di(aryl) cyclopentadienone is obtained from Morton Thiokol, Inc.

To the resulting suspension is slowly added with mixing anhydrous pyridine while maintaining a temperature below 0° C. and oxygen-free anhydrous conditions. The pyridine preferably has been purified by passage through 4 Å molecular sieves. The total amount of pyridine admixed is such as to achieve a mole ratio of pyridine to titanium tetrachloride of about 2:1 in the resulting suspension.

After the pyridine is added, mixing is preferably continued for at least about 24 hours to achieve complete reaction as the reaction mass is gradually warmed to ambient (room) temperature.

The reaction mass is then extracted, preferably by the addition thereto of both distilled or deionized water and a non-polar, water immersible organic solvent. Suitable organic solvents include ethers, such as diethyl ether; ketones, such as diethyl ketone; and the like. A two phase system results, one phase being aqueous, the other organic. Both phases are characteristically clear.

The organic phase is separated and preferably washed at least twice with dilute aqueous sodium bicarbonate solution and at least once with distilled or deionized water. Thereafter, the organic phase is dried; for example, with the aid of anhydrous magnesium sulfate, or the like, with the solvent being evaporated with the aid of a so-called rotovap unit, or the like. A solid is produced which characteristically has a deep purple color.

This solid can be dissolved, for further purification purposes, in a hydrocarbon, such as hexane or the like, and then the solution is subjected to flash chromatography, using, for example, a silica gel, or the like. The first eluted fraction contains the residual red colored starting material. The second and subsequent eluted fractions contain the deep purple product. The product fractions are evaporated and the purple solid recrystallized from acetonitrile, or the like, to yield a purified product identified as 1-dicyanomethylene-2,5-di(lower alkyl)-3,4-di(aryl) cyclopentadiene.

Since certain materials, such as 2,5-dimethyl-3,4-diphenyl cyclopentadienone, exist as a dimer, when such a material is employed, the molar ratio of each of the reagents used for reaction therewith is doubled. Also, in the case of such a material, the first eluted material from flash chromatography is the desired product which is then preferably recrystallized to produce the purified corresponding desired product, such as 1-dicyanomethylene-2,5-dimethyl-3,4-diphenyl cyclopentadiene.

Compounds of Formula (1) display useful electron transport capability when dissolved in an insulating organic binder polymer and formed into a charge transport layer of a photoconductor element. These compounds are particularly useful as electron-transport agents in positively-charged photoconductor elements.

A presently preferred class of photoconductor elements of this invention comprises:

(a) a substrate;
(b) an electrically conductive layer;
(c) a charge generation layer; and
(d) a charge transport layer comprising a polymeric binder containing at least one tetrasubstituted dicyanomethylene substituted cyclopentadiene of Formula (1).

Photoconductor elements of this invention display photosensitivity in the range of about 500 to about 900 nm, the exact photosensitivity achieved in a given photoconductor element being dependent upon the photoresponse characteristics of the charge generation layer employed therein. The term "photosensitivity" or "photo response" as used herein means the capacity, to be stimulated by light. For purposes of the present invention, photosensitivity is conveniently measured by charging the element to a certain potential, exposing the element to light and measuring the decrease of surface potential as the amount of energy necessary to discharge the element to a certain potential.

The photoconductor elements of this invention can employ conventional substrates, such as films or sheet materials as the support layer. The support layer is relatively thermally stable, electrically insulative, and has dielectric strength. Examples of polymers used in films include cellulose acetate, polystyrene, polycarbonates, polyesters, such as polyethylene terephthalate, and the like. Presently preferred substrates are polyethylene terephthalate and polycarbonates. Typical film type support layers have a thickness in the range of about 100 microns, although thicker and thinner layers can be employed.

The photoconductor elements of this invention can employ various electrically conductive layers. For example, the conductive layer can be a metal foil which is conventionally laminated to the support layer. Suitable metal foils include those comprised of aluminum, zinc, copper, and the like. The support layer and the conductive layer can be formulated as a consolidated layer which can be a metal plate, for example, suitable plates can be formed of metals, such as aluminum, copper, zinc, brass and galvanized steel. Alternatively, vacuum deposited metal layers upon a substrate are suitable and are presently preferred, such as deposited silver, nickel, gold, aluminum, chromium, and metal alloys. The thickness of a vapor deposited metal layer can be in the range of about 20 to about 500 Angstroms. Conductive layers can also comprise a particulate or dissolved organic or inorganic conductor or semi-conductor distributed in a binder resin. For example, a conductive layer can comprise compositions of protective inorganic oxide and about 30 to about 70 weight percent of conductive metal particles, such as a vapor deposited conductive cermet layer as described in U.S. Pat. No. 3,880,657 or U.S. Pat. No. 3,245,833 which relates to conductive layers employed with barrier layers. Organic conductive layers can be employed, such as those comprised of a sodium salt of a carboxyester lactone of maleic anhydride in a vinyl acetate polymer, as taught, for example in U.S. Pat. Nos. 3,007,901 and 3,262,807.

In the photoconductor elements of the invention, the conductive layer is optionally but preferably overcoated by a barrier adhesive or subbing layer. The barrier layer typically has a dry thickness in the range of about 0.01 to about 5 microns. Typical subbing layers are solvent soluble, film-forming polymers, such as, for example, cellulose nitrate, polyesters, copolymers of poly(vinyl pyrolidone) and vinylacetate, and various vinylidene chloride-containing polymers, including 2, 3 and 4 component polymers prepared from a polymerizable blend of monomers or prepolymers containing at least 60% by weight of vinylidene chloride. Representative vinylidene chloride-containing polymers include vinylidene chloride-methyl methacrylate-itaconic acid terpolymers such as disclosed in U.S. Pat. No. 3,143,421. Various vinylidene chloride-containing hydrogel tetrapolymers which may be used include tetrapolymers of vinylidene chloride, methyl acrylate, acrylonitrile and acrylic acid, such as disclosed in U.S. Pat. No. 3,640,780. Other useful vinylidene chloride-containing copolymers include poly(vinylidene chloride-methyl acrylate), poly(vinylidene chloride-methacrylonitryle), poly(vinylidene chloride-acrylonitrile), and poly(vinylidene chloride-acrylonitrile-methyl acrylate). Other subbing materials include the so called tergels described in U.S. Pat. No. 3,501,301 and the vinylidene chloride terpolymers described in U.S. Pat. No. 3,228,770. One useful class of subbing layers is comprised of a hydrophobic film-forming polymer or copolymer that is free from any acid-containing group, such as a carboxyl group, that is prepared from a blend of monomers or prepolymers, each of said monomers or prepolymers containing one or more polymerizable ethylenically unsaturated groups. Examples of such a polymer include many of the aforenamed copolymers, and, in addition, copolymers of polyvinylpyrrolidone and vinyl acetate, poly(vinylidene chloride-methyl methacrylate), and the like.

While any convenient method of application of a subbing layer can be used, it is presently preferred to dissolve the polymer in a solvent, and then to coat the solution over the conductive layer.

The barrier layer coating composition can also contain minor amounts of various optional additives, such as surfactants, levelers, plasticizers, and the like.

Mixtures of different solvents or liquids can be employed. Preferably, the solvents are volatile, that is, evaporable, at temperatures below about 150° C. Examples of suitable solvents include aromatic hydrocarbons, such as benzene, toluene, xylene, mesitylene, etc.; ketones, such as acetone, 2-butanone, etc.; ethers, such as tetrahydrofuran, methyl ethyl ether, petroleum ether, etc.; alkanols, such as isopropyl alcohol, etc.; halogenated aliphatic hydrocarbons, such as methylene dichloride, chloroform, and ethylene chloride, etc.; and the like. Presently preferred coating solvents are chlorinated aliphatic hydrocarbons.

The barrier layer coating composition is applied by using a technique such as knife coating (preferred), spray coating, swirl coating, extrusion hopper coating (preferred), or the like. After application, the coating composition is conveniently air dried.

The charge generation layer is applied over the conductive layer, or over the barrier layer, if a barrier layer is employed.

The charge generating (or generation) layer is conveniently comprised of at least one conventional photoconductor (or photoconductive agent) which is typically dispersed in a polymeric binder. The layer can have a thickness which varies over a wide range, typical layer thicknesses being in the range of about 0.05 to about 5 microns. As those skilled in the art appreciate, as layer thickness increases, a greater proportion of incident radiation is absorbed by a layer, but the likelihood increases of trapping a charge carrier which then does not contribute to image formation. Thus, an optimum thickness of a layer can constitute a balance between these competing influences.

Photoconductors suitable for use in the charge generating layer include organic compounds which exhibit photoconductivity. The term "photoconductivity" as used herein means the increase in electrical conductivity displayed by a non-metallic solid when it absorbs electromagnetic radiation. For purposes of this invention, a photoconductor in the dark is electrically insulating, but, upon exposure to actinic radiation, becomes electrically conductive. The dark resistivity of a photoconductor used in the practice of this invention is preferably greater than about $10^{11}$ ohm-centimeters (ohm-cm) at 25° C. and is rapidly reduced by several orders of magnitude when exposed to actinic radiation at an intensity of about 1 to about 30 ergs per sq. cm$^2$ per sec. (ergs/cm$^2$/sec). Typically and preferably, a charged photoconductor employed in the practice of this invention which is preliminarily charged to 500 volts discharges by at least 250 volts within 10 seconds when exposed to radiation at an energy level of 5 ergs/cm$^2$/sec using at least one wavelength in the range of about 400 to about 900 nm.

A wide variety of photoconductors can be employed, including inorganic, and organic photoconductors. Inorganic materials include, for example, zinc oxide, lead oxide, and selenium. Organic materials include various particulate organic pigment materials, such as phthalocyanine pigments, and a wide variety of soluble organic compounds including metallo-organic and polymeric organic photoconductors. A partial listing of representative photoconductive materials may be found, for example, in Research Disclosure, Vol. 109, May 1973, page 61, in an article entitled "Electrophotographic Elements, Materials and Processes".

Examples of suitable organic photoconductors include: Phthalocyanine pigments, such as a bromoindium phthalocyanine pigment described in U.S. Pat. No. 4,727,139 or a titanylphthalocyanine pigment described in U.S. Pat. No. 4,701,396; various pyrylium dye salts, such as pyrylium, bispyrylium, thiapyrylium, and selenapyrylium dye salts, as disclosed, for example, in U.S. Pat. No. 3,250,615; fluorenes, such as 7,12-dioxo-13-dibenzo (a,h) fluorene, and the like; aromatic nitro compounds of the kind disclosed in U.S. Pat. No. 2,610,120; anthrones such as those disclosed in the U.S. Pat. No. 2,670,284; quinones such as those disclosed in U.S. Pat. No. 2,670,286; benzophenones, such as those disclosed in U.S. Pat. No. 2,670,287; thiazoles, such as those disclosed in U.S. Pat. No. 3,732,301; various dyes such as cyanine (including carbocyanine, merocyanine, diarylmethane, thiazine, azine, oxazine, xanthene, phthalein, acridine, azo, anthraquinone dyes, and the like, and mixutures thereof.

The photoconductor, or mixture of photoconductors, is usually applied from a solution in a coating composition to form a charge generating layer in an element over a barrier layer of the type described herein. Also typically present as dissolved solids in a photoconductor layer coating composition are a binder polymer and optional additives.

In general, such compositions may be prepared by blending the components together in a solvent liquid.

As the binder polymer, any hydrophobic organic polymer known to the photoconductive element art can be used. These polymers are film forming and preferably organic solvent soluble, and, in solid form, display dielectric strength and electrical insulating properties. Suitable polymers include, for example, styrene-butadiene copolymers; polyvinyl toluene-styrene copolymers; silicone resins; styrene alkyd resins; silicone-alkyd resins; soya-alkyd resins; (vinyl chloride); poly (vinylidene chloride); vinylidene chloride-acrylonitrile copolymers; poly (vinyl acetate); vinyl acetate-vinyl chloride copolyers; poly (vinyl acetals), such as poly (vinyl butryl); polyacrylic and methacrylic esters, such as poly (methyl methacrylate, poly (n-butyl methacrylate), poly (isobutyl methacrylate), etc.; polystyrene; nitrated polystyrene; polymethylstyrene; isobutylene polymers; polyesters, such as poly [ethylene-co-isopropylidene-2,2-bis (ethylene-oxyphenylene) terephthalate]; copolymers of vinyl haloarylates and vinyl acetate, such as poly (vinyl-m-bromobenzoate-co-vinyl acetate); chlorinated polyolefins such as chlorinated polyethylene; and the like. Preferred polymers are polycarbonates and polyesters.

One or more electron donor agents can also be added, such as 1,1-bis(4-di-p-tolylaminophenyl) cyclohexane, as taught in U.S. Pat. No. 4,127,412, tri-p-tolylamine, and the like. Coating aids, such as levelers, surfactants, cross linking agents, colorants, plasticizers, and the like, can also be added. The quantity of each of the respective additives present in a coating composition can vary, depending upon results desired and user preferences. Presently preferred additives are electron donor agents and surfactants.

On a 100 weight percent total solids basis, the photoconductive layer coating composition comprises about 5 to about 10 weight percent photoconductor, about 0 to about 90 weight percent binder, and about 0 to about 40 weight percent total additives.

Instead of a photoconductive agent being dispersed in a polymeric binder, a charge generation layer can, in some cases, depending upon the photoconductive agent involved, be comprised substantially entirely of only such an agent. For example, a perylene dicarboximide pigment of the formula:

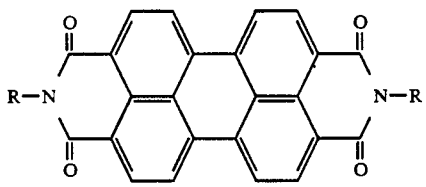

wherein R is an arylalkylene group;
can be applied over an electrically conductive layer under vacuum by sublimation, such as under subatmospheric pressures of about $10^{-2}$ to about $10^{-5}$ mm Hg at temperatures in the range of about 200 to about 400° C.

A photoconductive charge generating layer liquid coating composition is applied by coating the composition over the barrier layer using a technique such as above described for coating a barrier layer composition. After coating, the charge generating layer composition is conveniently air dried.

The charge transport layer is applied over the charge generation layer. When the charge transport layer contains at least one compound of Formula (1), an n-type charge transport layer is produced. An n-type charge transport layer accepts and transports negative charges (i.e., electrons).

A charge transport layer, if desired, can contain, in addition to at least one compound of Formula (1), at least one additional n-type charge transport agent of a type known to the prior art.

In the charge transport layer, the charge transport agent(s) are disperesed, and preferably dissolved, in an electrically insulating organic polymeric film forming binder. In general, any of the polymeric binders heretofore described for use can be used.

A present preference is to employ a binder such as poly[4,4′(2-norbornylidene)bisphenylene terephthalate-co-azelate] 60/40 in the practice of this invention.

On a 100 weight percent total solids basis, a charge transport layer preferably is comprised of about 10 to about 60 weight percent of at least one Formula (1) compound and about 20 to about 80 weight percent of binder. Typically, a charge transport layer has a thickness in the range of about 3 to about 12 microns, although thicker and thinner such layers can be employed.

Additionally, but optionally, a charge transport layer can incorporate an n-type charge transport agent known to the prior art, such an agent when present typically being employed in a charge transport layer on a total layer weight basis in an amount in the range of about 10 to about 40 weight percent.

Representative of suitable prior art n-type charge transport agents are strong Lewis acids, such as organic, including metallo-organic, compounds containing one or more aromatic, including aromatically unsaturated heterocyclic, groups bearing an electron-withdrawing substituent. These are useful because of their electron-accepting capability. Typical electron withdrawing substituents include cyano; nitro; sulfonate; halogens, such as chlorine, bromine and iodine; ketone groups; ester groups; acid anhydride groups and other acid groups, such as carboxyl and quinone groups. Representative n-type aromatic Lewis acids having electron-withdrawing substituents include phthalic anhydride, tetrachlorophthalic anhydride, benzil, mellitic anhydride, S-tricyanobenzene, picrylchloride, 2,4-dinitrochlorobenzene, 2,4-dinitrobromobenzene, 4-nitrobiphenyl, 4,4-dinitrobiphenyl, 2,4,6-trinitroanisole, trichlorotrinitrobenzene, trinitro-o-toluene, 4,6-dichloro-1,3-dinitrobenzene, 4,6-dibromo-1,3-dinitrobenzene, p-dinitrobenzene, chloranil, bormanil, 2,4,7-trinitro-9-fluorenone, 2,4,5,7-tetranitrofluorenone, trinitroanthracene, dinitroacridine, tetracyanopyrene, dinitroanthraquinone, and mixtures thereof.

Other useful n-type charge transports are conventional n-type organic photoconductors, for example, complexes of 2,4,6-trinitro-9-fluorenone. Still others are the n-type photoconductors described in Research Disclosure, Vol.109, May, 1973, pages 61-67, paragraph IV (a) (2)through(13).

A charge transport layer of this invention can be produced in bipolar form, if desired, by incorporating thereinto additionally at least one p-type transport agent. Such an agent preferentially accepts and transports positive charges (holes). A charge transport layer can contain more than one p-type charge transport or hole transport agent. If employed, the quantity of p-type transport agent(s) present in a charge transport layer on a total layer weight basis is preferably in the range of about 10 to about 50 weight percent, although larger and smaller such quantities can be employed, if desired.

Examples of suitable p-type organic charge transport agents known to the prior art include:

1. Carbazoles including carbazole, N-ethyl carbzole, N-isopropylcarbazole, N-phenyl carbazole, halogenated carbazoles, various polymeric carbazole materials such as poly(vinyl carbazole), halogenated poly(vinyl carbazole), and the like.

2. Arylamines including monoarylamines, diarylamines, triarylamines and polymeric arylamines. Specific arylamine organic photoconductors include the nonpolymeric triphenylamines illustrated in U.S. Pat. No. 3,180,730; the polymeric triarylamines described in U.S. Pat. No. 3,240,597; the triarylamines having at least one of the aryl radicals substituted by either a vinyl radical or a vinylene radical having at least one active hydrogen-containing group, as described in U.S. Pat. No. 3,567,450; the triarylamines in which at least one of the aryl radicals is substituted by an active hydrogen-containing group, as described by U.S. Pat. No. 3,658,520; and tritolylamine.

3. Polyarylalkanes of the type described in U.S. Pat. Nos. 3,274,000; 3,542,547; and 3,615,402. Preferred polyarylalkane photoconductors are of the formula:

wherein:
- D and G, which may be the same or different, each represent an aryl group, and
- J and E which may be the same or different, each represent hydrogen, an alkyl group, or an aryl group, and
- at least one of D, E and G contain an amino substituent.

An especially useful charge-transport material is a polyarylalkane wherein J and E are each hydrogen, aryl or alkyl, and D and G are each substituted aryl groups having as a substituent thereof a group of the formula:

wherein:
R is an unsubstituted aryl group, such as phenyl or alkyl-substituted aryl, such as a tolyl group. Examples of such polyarylalkanes may be found in U.S. Pat. No. 4,127,412.

4. Strong Lewis bases, such as aromatic compounds, including aromatically unsaturated heterocyclic compounds free from strong electron-withdrawing groups. Examples include tetraphenylpyrene, 1-methylpyrene, perylene, chrysene, anthracene, tetraphene, 2-phenyl naphthalene, azapyrene, fluorene, fluorenone, 1-ethylpyrene, acetyl pyrene, 2,3-benzochrysens, 3,4-benzopyrene, 1,4-bromopyrene, phenylindole, polyvinyl carbazole, polyvinylpyrene, polyvinyltetracene, polyvinyl perylene and polyvinyl tetraphene.

5. Hydrazones, including the dialkylsubstituted aminobenzaldehyde-(diphenylhydrazones) of U.S. Pat. No. 4,150,987; alkylhydrazones and arylhydrazones as described in U.S. Pat. Nos. 4,554,231; 4,487,824; 4,481,271; 4,456,671; 4,446,217; and 4,423,129, which are illustrative of the p-type hydrazones.

Other useful p-type charge transports are the p-type photoconductors described in Research Disclosure, Vol. 109, May, 1973, pages 61–67, paragraph IV (A) (2) through (13).

In addition to an n-type or a p-type prior art charge transport agent and a binder polymer, a charge transport layer of this invention may contain various optional additives, such as surfactants, levelers, plasticizers, and the like.

A presently preferred additive is a poly(dimethyl-co-methylphenyl siloxane) surfactant.

On a 100 weight percent total solids basis, a charge transport layer can contain up to about 15 weight percent of such additive and preferably about less than 1 weight percent of such additive.

The charge transport layer solid components are conveniently preliminarily dissolved in a solvent to produce a charge transport layer composition containing about 8 to about 15 weight percent solids with the balance up to 100 weight percent being the solvent. The solvents are as hereinabove described.

Coating of the charge transport layer composition over the charge generation layer can be accomplished using a coating technique such as hereinabove indicated. After coating, this charge transport layer composition is conveniently air dried.

If desired, a charge transport layer can be formed of two or more successive layers each of which has a different total solids composition. In such an event at least one of such charge transport sublayers contains at least one compound of Formula (1).

Preferred photoconductor elements of this invention characteristically display dark decay values of not more than about 12 V/sec.

The term "dark decay" as used herein means the loss of electric charge from a charged photoconductor element under dark conditions and in the absence of activating radiation.

For present purposes of measuring dark decay, a multilayered photoconductor element of the type under consideration herein is charged upon its charge transport layer with a positive charge in the range of about 400 to about 600 volts. Thereafter, the rate of charge dissipation in volts per second is measured. The element is preliminary dark adapted and maintained in the dark without activating radiation during the evaluation using ambient conditions of temperature and pressure.

Those skilled in the art will appreciate that other variations in the structure of photoconductor elements incorporating a charge transport layer containing a compound of Formula (1) are possible and practical. For example, various different layer arrangements can be employed. Thus, a transport layer can be positioned, or "sandwiched", between two charge generation layers which can have the same or different respective compositions and layer thicknesses. Also, a charge generation layer can be positioned between two charge-transport layers only one of which may contain a compound of Formula (1).

The invention is further illustrated by the following Examples:

EXAMPLE 1

Preparation of 1-dicyanomethylene-2,5-diethyl-3,4-diphenylcyclopentadiene (2a)

A one-liter, 3-necked round-bottom flask equipped with a mechanical stirrer, a 125 mL pressure-equalizing additional funnel and a Y-tube with a rubber septum and $N_2$ inlet, was flushed for 5 minutes with $N_2$. Approximately 200 mL of distilled tetrahydrofuran (THF) was added to the flask which was then cooled to 0° C. with an ice-water bath. Fifty mL of dry carbon tetrachloride (4 Å molecular sieves) was poured into the additional funnel under a stream of nitrogen. The system was then closed to maintain it under an nitrogen atmosphere. Twenty-two mL (0.2 mole) of titanium tetrachloride was syringed into the carbon tetrachloride in the additional funnel and the resultant solution added dropwise to the vigorously stirred, chilled THF. To the resulting yellow precipitate was rapidly added via transfer needle, a 150 mL solution of distilled THF containing 28.8 g (0.1 mole) 2,5-diethyl-3,4-diphenyl cyclopentadienone (purchased from Morton Thiokol, Inc.) and 6.6 g (0.1 mole) of distilled malonitrile (110° C., 20 Torr). The resultant brown suspension was stirred at 0° C. for 20 minutes after which time 32.4 mL (0.4 mole) of dry pyridine (4 Å molecular sieves) was syringed into the addition funnel and added dropwise over 20 minutes. The suspension was allowed to warm to room temperature overnight and then stirred for an additional 48 hours. Two hundred mL of water and 100 mL diethyl ether were added resulting in two clear phases. The organic phase was separated and washed twice with 200 mL dilute sodium bicarbonate solution and once with 100 mL water. The organic phase was dried with the aid of $MgSO_4$ and the solvent rotavaporated to yield a deep purple solid which was dissolved in 80 mL hexane and flash chromatographed (silica gel, 4×50 cm) with hexane. The first eluted fraction contains the red starting material, followed by the deep purple product. The product fractions were evaporated and the purple solid recrystallized from acetonitrile to yield 6.2 g (18.4%) 1-dicyanomethylene-2,5-diethyl-3,4-diphenyl cyclopentadiene (2a): mp 154°-6° C.; field desorption mass spectrum m/e 336 (M+); $^1$H NMR (CDCl$_3$): δ 1.2 (t, 6H), 2.6 (q, 4H), 6.8 (m, 4H), 7.2(m,6H); $E^{\frac{1}{2}} = -0.59$ V vs SCE (reversible); $_{max}$ 407, 547 nm CHCl$_2$. Anal. Calcd. for $C_{24}H_{20}N_2$: C, 85.7; H, 6.0; N, 8.3. Found C, 85.5; H, 6.0; N, 8.3

EXAMPLE 2

Preparation of
1-Dicyanomethylene-2,5-dimethyl-3,4-diphenyl-cyclopentadiene)

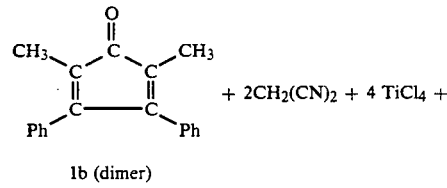

1b (dimer)

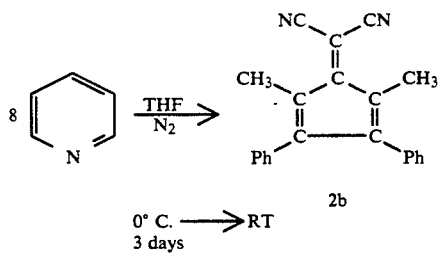

2b

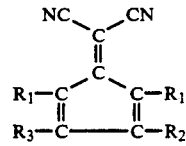

3 days

The dimethyl derivative 2b was prepared from 1b in the manner of Example 1, except that the molar ratio of all reagents except 1b was doubled. During flash chromatography with hexane, the first eluted material is the desired product which, when recrystallized from acetonitrile, gave a 5.5% yield of 1-dicyanomethylene-2,5-dimethyl-3,4-diphenylcylopentadiene (2b): m.p. 165°-6° C., field desorption mass spectrum m/e 308 (M+); $^1$H NMR (CDCl$_3$): δ 2.26 (s, 6H); 6.86 (m, 4H); 7.24 (m,6H). Anal. Calcd for $C_{22}H_{16}N_2$: C, 85.0; H, 5.2; N, 9.0. Found: C, 85.7; H, 5.2; N, 9.1.

EXAMPLE 3

A 0.1 μm thick bromoindium phthalocyanine charge-generation layer was prepared on a conductive nickel-coated poly(ethylene-terephthalate) film support by vacuum sublimation from a resistance-heated tantalum boat at a rate of 20 Å/sec. A 5 μm thick charge-transport layer containing (2a) 1-dicyanomethylene-2,5-diethyl-3,4-diphenyl cyclopentadiene (30%) and poly[4,4'-(2-norbornylidene)bisphenylene terephthalateco-azelate]60/40 binder (70%) was coated over the charge generation layer from chloroform. The electro photographic response of the film was measured by charging the element to 500 V with a corona charger in the dark. After 1 second a monochromatic light was turned on and the element was exposed to light of 5 ergs/cm$^2$/sec intensity.

The sensitivity (S) was 31 ergs/cm$^2$ for discharge from 500 V to 250 V at 830 nm.

EXAMPLE 4

A charge-generation layer was prepared as described in Example 3 and was over coated with a charge transport layer of about 5 μm comprising compound (2b)1-dicyanomethylene-2,5-dimethyl-3,4-diphenylcyclopentadiene (37%) and poly[4,4'-2(-norbornylidene)bisphenylene terephthalate-co-azelate]40/60 binder (63%) from chloroform. The resulting photoreceptor was tested as described in Example 3 and the sensitivity(S,830 nm)for discharge from 500 V to 250 V was 30 ergs/cm$^2$.

The foregoing specification is intended as illustrative and is not to be taken as limiting. Still other variations within the spirit and the scope of the invention are possible and will readily present themselves to those skilled in the art.

We claim:

1. A compound of the formula:

$$\begin{array}{c} NC \diagdown_{C} \diagup CN \\ \| \\ C \\ R_1-C \diagup \diagdown C-R_1 \\ \| \quad \| \\ R_3-C-----C-R_2 \end{array}$$

wherein R$_1$ and R$_4$ are individually selected from the group consisting of lower alkyl, halogen and cyano, and where R$_2$ and R$_3$ are each aryl.

2. The compounds of claim 1 wherein R$_1$ and R$_4$ are each selected from the group consisting of methyl, ethyl, and n-propyl.

3. The compounds of claim 1 wherein the aryl group is substituted by a group selected from lower alkyl, lower alkylene, nitro, halo, primary, secondary or tertiary amino, cyano and sulfate.

* * * * *